United States Patent
Yoshihara et al.

(10) Patent No.: US 7,393,542 B2
(45) Date of Patent: Jul. 1, 2008

(54) REMEDIES FOR ALLERGIC DISEASES USING PROCESSED PEANUT SEED COAT

(75) Inventors: Akio Yoshihara, 13-23-804, Nishiazabu 4-chome, Minato-ku, Tokyo 106-0031 (JP); Tomihisa Ohta, Ishikawa (JP); Takahiro Moro, Saitama (JP); Kaoru Hirose, Chiba (JP)

(73) Assignees: Akio Yoshihara, Tokyo (JP); Sachiko Yoshihara, Tokyo (JP)

( * ) Notice: Subject to any disclaimer, the term of this patent is extended or adjusted under 35 U.S.C. 154(b) by 496 days.

(21) Appl. No.: 10/487,899

(22) PCT Filed: Feb. 15, 2002

(86) PCT No.: PCT/JP02/01326

§ 371 (c)(1), (2), (4) Date: Feb. 26, 2004

(87) PCT Pub. No.: WO03/020295

PCT Pub. Date: Mar. 13, 2003

(65) Prior Publication Data

US 2004/0247712 A1    Dec. 9, 2004

(30) Foreign Application Priority Data

Aug. 31, 2001 (JP) ............................. 2001-263795

(51) Int. Cl.
*A61K 36/48*    (2006.01)

(52) U.S. Cl. .................. 424/275.1; 424/439; 424/440; 424/757; 424/776

(58) Field of Classification Search ........................ None
See application file for complete search history.

(56) References Cited

U.S. PATENT DOCUMENTS 6,258,361 B1    7/2001   Yoshihara et al.

FOREIGN PATENT DOCUMENTS

| CN | 1323776 A | | 11/2001 |
|---|---|---|---|
| JP | 07010765 A | * | 1/1995 |
| JP | 10-120588 A | | 5/1998 |
| JP | 11-246431 A | | 9/1999 |
| JP | 11-246562 A | | 9/1999 |
| JP | 11-246562 A | | 9/1999 |
| JP | 2000143528 A | * | 5/2000 |
| JP | 2000178196 A | * | 6/2000 |
| JP | 2001-247428 A | | 9/2001 |

OTHER PUBLICATIONS

Pucar, F. et al. Clinical and Experimental Allergy (2001), 31(1): 40-46. Peanut challenge: a retrospective study of 140 patients.*
Machine Translation of JP 112246562 A.*
McEwen, LM et al. British Medical Journal, May 20, 1967; 2(5550):507-508. Hyaluronidase in the treatment of allergy.*
Zhang et al., Zhongguo Zhong Yuao Za Zhi. Jun. 1990; 15(6):365-8, 384 (English Abstract only).
Physiological Activity Function of Peanut Seed Coat, *Journal of Cereals & Oils*, No. 4, pp. 44-45, Apr. 10, 2001 (w/English translation).
H. Lou et al., *Phytochemistry*, vol. 51 (1999) pp. 297-308.

* cited by examiner

*Primary Examiner*—Michele Flood
(74) *Attorney, Agent, or Firm*—Birch, Stewart, Kolasch & Birch, LLP

(57) ABSTRACT

An agent for treating or preventing allergic disease comprising, as an active ingredient, a treated product of peanut seed coats.

2 Claims, 1 Drawing Sheet

REMEDIES FOR ALLERGIC DISEASES USING PROCESSED PEANUT SEED COAT

TECHNICAL FIELD

The present invention relates to an agent for treating or preventing allergic disease comprising a peanut seed coat-derived active ingredient.

BACKGROUND ART

Pollinosis exhibits symptoms such as sneezing or continuous sniveling due to aspiration of pollens, and causal factors thereof have not completely been clarified yet. Since pollinosis occurs frequently in urban areas, there are hypotheses that dust or metallic fines are involved, or that reduction of parasites is a contributing factor. In respect of the onset mechanism, pollinosis is an anaphylactic reaction, and the onset of pollinosis is explained by release of inflammatory substances caused by binding of an antigen and IgE to a mastocyte (mast cell) in a bridge form. Presently, as a treatment method for pollinosis medically, there are medically used administration of an antihistaminic agent, oral immunologic tolerance method and the like, but these methods are not conclusive. Generally, methods such as use of a mask or a device to prevent aspiration of pollens are applied, but these methods are not very effective.

For treatment of allergic disease such as pollinosis, allergic rhinitis, atopic dermatitis or bronchial asthma, a steroid agent is broadly used, but this agent is desirably used in the short term because of the problem of side effects. However, where the use of a steroid agent is stopped, it results in a deterioration of the symptoms and, in some cases, what is called a rebound phenomenon may occur, wherein the symptom becomes worse than before the use of the steroid agent.

A treated product of peanut seed coats is known to have bone marrow cell-proliferating activity, anti-HIV activity, etc. (Japanese Patent Application Laying-Open (Kokai) Nos. 10-120588 and 11-246431, but there are no reports regarding antiallergic activity.

DISCLOSURE OF THE INVENTION

The object of the present invention is to provide an agent effective for treatment or prevention of allergic disease.

That is to say, the present invention includes the following inventions.

(1) An agent for treating or preventing allergic disease comprising, as an active ingredient, a treated product of peanut seed coats.

(2) The agent for treating or preventing allergic disease according to (1) above, wherein the treated product of peanut seed coats is an extract from peanut seed coats or a treated product thereof.

(3) The agent for treating or preventing allergic disease according to (2) above, wherein the extract from peanut seed coats is a water extract.

(4) An agent for treating or preventing allergic disease comprising, as an active ingredient, a water-soluble substance derived from peanut seed coats.

(5) An agent for treating or preventing allergic disease comprising, as an active ingredient, a lower alcohol-soluble substance derived from peanut seed coats.

(6) An agent for treating or preventing allergic disease comprising, as an active ingredient, a water- and lower alcohol-soluble substance derived from peanut seed coats.

(7) The agent for treating or preventing allergic disease according to any one of (1) to (6) above, which is used to add to a food, chewing gum or drink.

(8) The agent for treating or preventing allergic disease according to any one of (1) to (7) above, wherein the allergic disease is pollinosis, allergic rhinitis, atopic dermatitis or bronchial asthma.

(9) A method for treating or preventing allergic disease, which comprises administering a pharmaceutical composition, food, chewing gum or drink comprising a treated product of peanut seed coats, to a subject.

The fruit of peanut has a solid pericarp, and usually there are two seeds inside the pericarp. These seeds are covered with seed coats. In the present invention, these seed coats are used.

In the present invention, a peanut seed coat may be used as a powdered product obtained by crushing, pulverization etc., but the use as an extract or a treated product thereof is preferable.

Examples of an extraction solvent include water; lower alcohols such as methanol, ethanol, propanol, isopropanol, butanol and isobutanol; ethers such as ethyl ether and dioxane; ketones such as acetone, but water, ethanol or a mixed solvent of water and ethanol is preferable.

In extraction, peanut seed coats may be used with no treatment, or alternatively they may be crushed or powdered to give greater contact with a solvent.

Waste water obtained in the process of separating peanut seed coats from peanut seeds by washing with water, and then purified or dried, if necessary, may be used as an extract, but preferably 1 kg of peanut seed coats is extracted with 5 to 25 L of solvent.

Extraction temperature is not particularly limited, and usually ranges from room temperature to the boiling point of the solvent under ordinary pressure. The extraction period varies depending on extraction temperature or the like, but is preferably one day.

The thus obtained extract may directly be used as an active ingredient of the agent for treating or preventing allergic disease of the present invention. Alternatively, the extract may be used as a treated product with higher activity after undergoing a treatment by various purification means such as ion exchange chromatography, gel filtration chromatography and dialysis. In this case, purification is preferably carried out by utilizing chemical properties of an active ingredient. That is to say, the preferred active ingredient of the agent for treating or preventing allergic disease of the present invention has a property of dissolving in water and/or lower alcohol (e.g. ethanol), and so, using this property, an active ingredient with a higher purity can be obtained by collecting a substance with solubility in water, a substance with solubility in lower alcohol, or a substance with solubility in water and lower alcohol.

The agent for treating or preventing allergic disease of the present invention can be formulated into pharmaceutical preparations by using a treated product of peanut seed coats in combination with a known pharmaceutical carrier. The dosage form is not particularly limited and may be selected as appropriate, but generally the agent of the present invention is used as an oral agent such as a tablet, capsule, granule, fine granule, powder, solution, syrup, suspension, emulsion or elixir, or a parenteral agent such as an injection, drop, suppository, inhalant, percutaneous absorption agent, permucosal absorption agent or poultice.

The dosage of the agent for treating or preventing allergic disease of the present invention varies depending on a patient's age, weight, degree of the disease, or administration route. In oral administration, the dosage of the agent ranges usually from 50 to 1,000 mg per day as a dry powder of a peanut seed coat extract, and frequency of administration is once to three times a day in oral administration.

Such oral agents are prepared by conventional methods, using an excipient such as starch, lactose, sucrose, mannitol, carboxymethylcellulose, corn starch or inorganic salts.

In such preparations, binders, disintegrants, surfactants, lubricants, fluidity promoters, flavoring agents, coloring agents, perfumes or the like may also be used as appropriate in addition to the above-stated excipients.

Examples of binders may include crystalline cellulose, crystalline cellulose/carmellose sodium, methylcellulose, hydroxypropylcellulose, hydroxypropylcellulose with a low degree of substitution, hydroxypropylmethylcellulose, hydroxypropylmethylcellulose phthalate, hydroxypropylmethylcellulose acetate succinate, carmellose sodium, ethylcellulose, carboxymethylethylcellulose, hydroxyethylcellulose, wheat starch, rice starch, corn starch, potato starch, dextrin, gelatinized starch, partially gelatinized starch, hydroxypropylstarch, pullulan, polyvinylpyrrolidone, aminoalkyl methacrylate copolymer E, aminoalkyl methacrylate copolymer RS, methacrylate copolymer L, methacrylate copolymer S, methacrylate copolymer LD, polyvinyl acetal diethyl aminoacetate, polyvinyl alcohol, acacia, powdered acacia, agar, gelatin, white shellac, tragacanth gum, purified sucrose, macrogol 200, macrogol 300 and macrogol 6000.

Examples of disintegrants may include crystalline cellulose, methylcellulose, hydroxypropylcellulose with a low degree of substitution, carmellose, carmellose calcium, carmellose sodium, cross-carmellose sodium, wheat starch, rice starch, corn starch, potato starch, partially gelatinized starch, hydroxypropyl starch, sodium carboxymethyl starch and tragacanth gum.

Examples of surfactants may include soybean lecithin, sucrose fatty acid esters, polyoxyl stearate 40, polyoxyethylene hardened castor oil 100, polyoxyethylene hardened castor oil 40, polyoxyethylene hardened castor oil 50, polyoxyethylene hardened castor oil 60, polyoxyethylene[42] polyoxypropylene[67]glycol, polyoxyethylene[54] polyoxypropylene[39]glycol, polyoxyethylene[105] polyoxypropylene[5]glycol, polyoxyethylene[160] polyoxypropylene[80]glycol, polyoxyethylene[196] polyoxypropylene[67]glycol, sorbitan sesquioleate, sorbitan trioleate, sorbitan monostearate, sorbitan monopalmitate, sorbitan monolaurate, polysorbate 40, polysorbate 60, polysorbate 65, polysorbate 80, glycerol monostearate, sodium lauryl sulfate and lauromacrogol.

Examples of lubricants may include wheat starch, rice starch, corn starch, stearic acid, calcium stearate, magnesium stearate, hydrous silicon dioxide, light anhydrous silicic acid, synthetic aluminium silicate, dry aluminium hydroxide gel, talc, magnesium aluminate metasilicate, calcium hydrogenphosphate, anhydrous calcium hydrogenphosphate, sucrose fatty acid esters, waxes, hydrogenated vegetable oils and polyethylene glycol.

Examples of fluidity promoters may include hydrous silicon dioxide, light anhydrous silicic acid, dry aluminium hydroxide gel, synthetic aluminium silicate and magnesium silicate.

Where the agent for treating or preventing allergic disease of the present invention is administered as a solution, syrup, suspension, emulsion or elixir, it may contain a flavoring agent or coloring agent.

The agent for treating or preventing allergic disease of the present invention may be added to food, chewing gum, drinks or the like to produce what is called a specified supplement food.

The agent for treating or preventing allergic disease of the present invention is useful for treatment or prevention of various allergic diseases such as pollinosis, allergic rhinitis, atopic dermatitis and bronchial asthma.

Peanut seed coats, which are raw materials for the production of the agent for treating or preventing allergic disease of the present invention, have been served as food together with peanut seeds, and so the safety of this material has been established.

Figure 1:
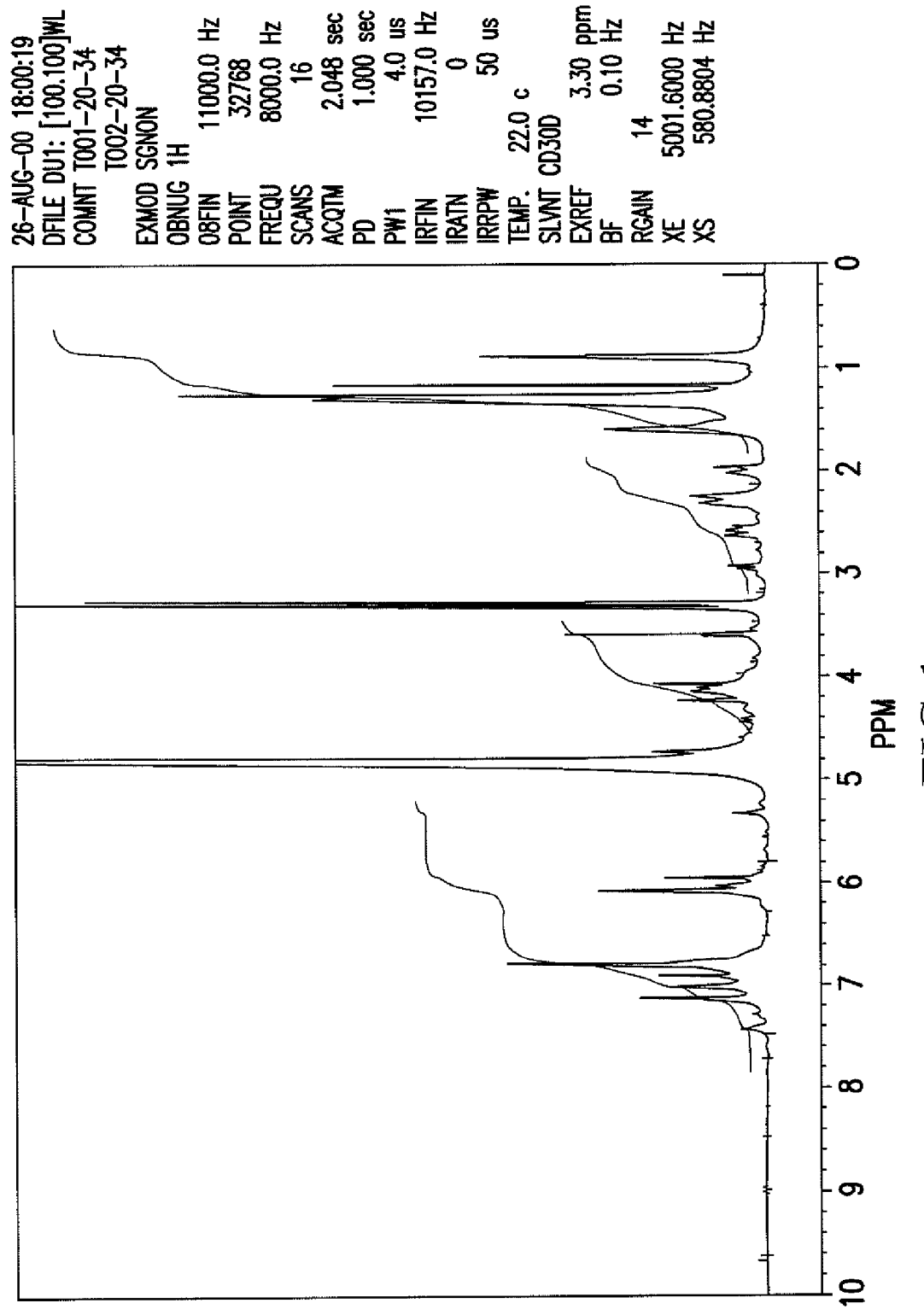
FIG. 1 is a figure showing a nuclear magnetic resonance spectrum of an extract from peanut seed coats.

This specification includes the contents as disclosed in the specification of Japanese Patent Application No. 2001-263795, which is a priority document of the present specification.

BEST MODE FOR CARRYING OUT THE INVENTION

The present invention is further described in the following examples. However, the examples are not intended to limit the scope of the invention.

Example 1

(1) Preparation of Extract from Peanut Seed Coats

The seeds of peanut (*Arachis hypogaea* L., Leguminosae) produced in China were dried for about a month, and then seed coats thereof were separated. Twenty-five grams of the dried seed coats was weighed accurately and placed in a 2 liter Erlenmeyer flask. One liter of purified water was added thereto and allowed to stand at room temperature ($22\pm3°$ C.) for 24 hours. The resultant mixture was filtered with a filter cotton, and the filtrate was freeze-dried to thereby obtain peanut seed coat extract powder (yield: 4.4484 g per 25 g of peanut seed coats). This powder is a hygroscopic, reddish-brown, fine powder without smell and with a bitter taste. This powder is readily soluble in both water and ethanol.

The nuclear magnetic resonance spectrum of a peanut seed coat extract is shown in FIG. 1. From the nuclear magnetic resonance spectrum, it is predicted that the main ingredient of a peanut seed coat extract is polyphenol.

(2) Human Clinical Data with Peanut Seed Coat Extract

The peanut seed coat extract powder obtained in (1) stated above was dissolved in mineral water, and the obtained solution was orally administered to allergic disease patients, and then progress was observed.

(Case A)

The patient suffered from pollinosis for 20 years. The patient had a stuffed nose and can breathe only through the mouth from the middle of February to the end of the consecutive holidays of May every year. The patient also has extremely itchy eyes and severe eye congestion. The patient had been suffering from various symptoms such as having itching even inside the ear.

From around Feb. 14, 2001, when the symptoms of pollinosis appeared, 500 mg of peanut seed coat extract powder was dissolved in 1,500 ml of mineral water, and the patient began administration of the peanut seed coat extract powder at a pace of 500 mg for 3 days. On the first day, there was no remarkable change, but after 2 or 3 days, symptoms were considerably eased, and after 1 week, the symptoms such as a stuffed nose or itchy eyes almost disappeared. Upon arising in the morning, some symptoms continued to appear for several days, but such symptoms disappeared after a short time by administration of the peanut seed coat extract powder solution.

Where the patient did not take the peanut seed coat extract powder solution for about a half a day, stuffed nose or itchy eyes reappeared. After administration of the solution, however, such symptoms were relieved. At first, it was effective to administer a small amount (about 100 ml) of the solution every 2 or 3 hours.

After about 1 month, although the dosage was slightly reduced, the symptoms did not appear. Moreover, the pace of administering the extract powder was also reduced to once in the morning, noon and evening (100 mg of peanut seed coat extract powder per day), but there was no appearance of symptoms.

(Case B)

The patient suffered from itchy eyes and a snivel caused by pollinosis from the beginning of February to the end of April for about 10 years. The patient was administered with injections for pollinosis when the symptoms were severe, but out of a concern for side effects, the patient stopped administration of the injection 3 years ago.

From Feb. 22, 2001, 500 mg of peanut seed coat extract powder was dissolved in 1,500 ml of mineral water, and the patient began administration of the peanut seed coat extract powder at a pace of 500 mg for 3 days.

On the first day, the patient did not feel any particular effect, but itchiness of the eyes had subsided on the $2^{nd}$ day, and almost no itching was felt on the $3^{rd}$ day. Before administration of the peanut seed coat extract powder solution, the patient had continuous sneezing upon arising in the morning. After administration, however, both sneezing and sniveling stopped. The patient had administered the peanut seed coat extract powder solution for about half-month, and then stopped administration, but the symptoms of pollinosis did not appear.

(Case C)

From around the spring of 1984, the patient had marked symptoms of pollinosis (itchy eyes and stuffed nose). However, since pollinosis had not been recognized yet in those days, the patient had been diagnosed as having allergic rhinitis. Around 1990, as pollinosis was publicly recognized, the patient was diagnosed as having severe pollinosis. The patient treated the symptoms such as itchy eyes and stuffed nose with an agent. Due to a side effect of "being drowsy", the patient had poor concentration at work and had had a continuously hard life.

In February, 2001, since the patient had marked symptoms of pollinosis, the patient visited to the hospital once a week and relied on a treatment with an agent as in previous years.

From Mar. 16, 2001, the patient began administration of a bottle of peanut seed coat extract powder solution obtained by dissolving 500 mg of peanut seed coat extract powder in 1,500 ml of mineral water, with the dosage shown in Table 1.

TABLE 1

| Date | Dosage (bottle) | State |
| --- | --- | --- |
| Mar. 16, 2001 | 1 | Symptoms such as severe itchiness of the eyes and stuffed nose appeared as a result of termination of the administration of the agent. |
| Mar. 17, 2001 | 1 | Suffered from the same severe symptoms as the previous day. |
| Mar. 18, 2001 | 1 | Itchiness of the eyes was slightly alleviated. |
| Mar. 19, 2001 | 0.5 | Symptoms were gradually alleviated, though that level was subtle. |
| Mar. 20, 2001 | 0.5 | Ditto |
| Mar. 21, 2001 | 0.5 | Ditto |
| Mar. 22, 2001 | 0.5 | Ditto |
| Mar. 23, 2001 | 0.5 | Ditto |
| Mar. 24, 2001 | 0.5 | Ditto |
| Mar. 25, 2001 | 0.5 | Ditto |
| Mar. 26, 2001 | 0.5 | Ditto |
| Mar. 27, 2001 | 1 | Remarkable signs of improvement appeared. The state of the nose had improved in the afternoon and sense of taste had returned. |
| Mar. 28, 2001 | 1 | The state of the nose and throat had further improved. |
| Mar. 29, 2001 | 1 | |
| Mar. 30, 2001 | 1 | |
| Mar. 31, 2001 | 1 | The symptoms of pollinosis almost completely disappeared. |
| Apr. 1, 2001 | 1 | |
| Apr. 2, 2001 | 1 | |
| Apr. 3, 2001 | 1 | Though pollen levels were high, the patient had only slightly itchy eyes and did not suffer very much therefrom. |
| Apr. 4, 2001 | 1 | Ditto |
| Apr. 5, 2001 | 1 | Though pollen levels were high, the patient's state was normal. |
| Apr. 6, 2001 | 1 | |
| Apr. 7, 2001 | 1 | |

As stated above, since severe symptoms of pollinosis were alleviated with no side effects, the patient was able to maintain a will to work.

(Case D)

In February of this year (2001), the patient was suddenly affected with pollinosis. At first, the patient only had a snivel and did not have symptoms such as sneezing or itchy eyes. As time passed, there appeared symptoms such as sneezing, itchy eyes, and pain due to sniveling, as if water had entered inside the nose. The patient had inflammation and pain under the nose, because the patient blew the their nose all day. So, the patient took a commercially available drug for rhinitis. The rhinitis was thereby alleviated, but the patient had strong nausea, dry mouth, drowsiness, etc., instead. Consequently, the patient stopped administration of the drug.

Then, the patient began administration of peanut seed coat extract powder.

At first, 500 mg of peanut seed coat extract powder was dissolved in 1,500 ml of mineral water, and the patient was administered with about 50 ml of the peanut seed coat extract powder solution. After a while, sniveling stopped, and then pain, as if water had entered inside the nose, sneezing and itchy eyes disappeared. Nausea, dry mouth and drowsiness that had appeared when the patient had taken a commercially available drug, did not appear at all. Since symptoms of pollinosis appeared again after about 3 hours, the patient repeatedly took the same amount of the peanut seed coat extract solution. After a while, duration of the extract solution prolonged from 3 hours to 4, and then 5 hours, and in the end, symptoms of pollinosis disappeared by administration only in the morning.

(Case E)

A 47-Year-Old Male

In Mar. 8, 2001, the male patient had pustule appear on the hands and feet due to chronic atopic dermatitis. The patient administered an antihistaminic agent and a vitamin preparation orally, and also used a steroid ointment.

From around May of 2001, the symptom became significantly clear. So, the patient was administered with an intravenous injection of steroid at times, and thereby the symptom was improved temporarily and the patient seemed to recover. However, the symptom was come out again and became worse than before.

In July, 2001, 500 mg of peanut seed coat extract powder was dissolved in 1,500 ml of mineral water to prepare an aqueous solution, and the patient was administered with 500 ml of the solution per day, divided over three times. After that, the patient stopped the steroid injection while taking the aqueous solution from the peanut seed coat extract powder every day. The symptom was thereby improved.

| Data of May 2001 | | |
|---|---|---|
| IgE | 740 IU/ml | |
| Eosinophil | 20% | Leukogram |
| Neutrophil | 40% | Leukogram |
| Data of September 2001 | | |
| IgE | 520 IU/ml | |
| Eosinophil | 15% | |
| Neutrophil | 43% | |

(Case F)

A 25-Year-Old Female

The female patient had generalized atopic dermatitis from when she was 15 years old. She treated the atopic dermatitis with a Chinese herbal medicine and a Chinese herbal ointment, but since the symptom was deteriorated from around November 2000, she could not even go to work, and so she was depressed. Consequently, she was administered also with an intravenous injection of steroid at times. She also used a steroid ointment.

Symptoms improved temporarily, but then reappeared again and again. So, the patient stopped administration of the steroid agent in April, 2001. Five hundred mg of peanut seed coat extract powder was dissolved in 1,500 ml of mineral water to prepare an aqueous solution, and the patient began administration of 500 ml of the solution per day, divided over three times.

Around November 2001, the symptom was alleviated, and then she did not have reappearance of the disease.

| Data of April 2001 | |
|---|---|
| IgE | 950 IU/ml |
| Eosinophil | 36% |
| Neutrophil | 43% |
| Lymphocyte | 15% |
| Data of August 2001 | |
| IgE | 430 IU/ml |
| Eosinophil | 25% |

| -continued | |
|---|---|
| Neutrophil | 45% |
| Lymphocyte | 20% |

(Case G)

A 57-Year-Old Female

This female patient has suffered from pollinosis for a long time, and in July 2000, she had also atopic dermatitis appeared. She had a good treatment progress for a while, using an ointment without steroid.

In April 2001, since both atopic dermatitis and pollinosis deteriorated, the patient was administered with a steroid ointment and orally with a steroid agent. The symptoms thereby subsided. Around September, however, the symptoms became worse than before, and so the patient stopped administration of the steroid ointment and the steroid agent. Five hundred mg of peanut seed coat extract powder was dissolved in 1,500 ml of mineral water to prepare an aqueous solution, and the patient began administration of 500 ml of the solution per day, divided over three times. Then, the symptoms disappeared.

Data of 2001

IgE 650 IU/ml,

Strongly positive to both house dust and mites

Data of November, 2001

IgE 500 IU/ml,

Leukogram was normal.

(Case H)

A 58-Year-Old Female

This patient had undergone treatment for bronchial asthma and atopic dermatitis for a long time. She was treated with a bronchodilator, an antiitussive agent and an inhalant.

In 2001, the skin symptoms deteriorated, and so the patient was administered with a steroid agent.

The symptom disappeared temporarily, but since atopic dermatitis and asthmatic attack became severe in September of 2001, the patient stopped administration of all agents. Five hundred mg of peanut seed coat extract powder was dissolved in 1,500 ml of water to prepare an aqueous solution, and the patient began administration of 500 ml of the solution per day, divided over three times. Symptoms of both atopic dermatitis and asthma were alleviated. The patient is in a good state still now.

Data of January, 2001

IgE 450 IU/ml

Data of October, 2001

IgE 400 IU/ml (Case I)

A 21-Year-Old Female

This patient suffered from bronchial asthma from when she was about 9 years old. From about 4 years ago, symptoms deteriorated. She suffered from severe attacks and was admitted to hospital 4 or 5 times every year. The dosage of agents increased year by year, and she suffered deeply from side effects of the agents used such as trembling hands, palpitation, sleeplessness and dysfunctional uterine bleeding.

Prednine (5 mg) tablets (adrenal cortical hormone):

One tablet was administered in the morning and another tablet at night for 12 years.

Spiropent tablets (bronchodilator):

One tablet was administered in the morning and another tablet at night for 12 years.

Theodur (200 mg) tablets (bronchodilator):

One tablet was administered in the morning and another tablet at night for 12 years.

Mucosolvan tablets (expectorant):

One tablet was administered in the morning, noon and evening for 10 years.

One bottle (13.5 ml) of Sultanol inhaler (bronchodilator) was administered for 12 years.

One bottle of Aldecin 100D (steroid inhalant) was administered for 12 years.

Singulair 10 (prevention of asthma) was administered at night for about 10 years.

One Cravit tablet (macrolide antibiotic; used only when bronchitis appeared) was administered in the morning, noon and evening one to three times per year for 4 years.

In September 2001, the patient had a severe attack, and also suffered from trembling hands, palpitation, and sleeplessness that were side effects of the agents used, and particularly, the patient had continuous dysfunctional uterine bleeding for 2 months.

The patient stopped administration of all agents. Then, 500 mg of peanut seed coat extract powder was dissolved in 1,500 ml of mineral water to prepare an aqueous solution, and the patient began administration of 500 ml of the solution per day, divided over three times. From the first day, the patient was relieved from suffering from asthma, and after 3 days, dysfunctional uterine bleeding terminated. Moreover, allergic rhinitis also disappeared, and there appeared no symptoms of asthma until January 2002. Even though the patient had cold, no symptoms appeared.

Steroid agents (external use, oral administration, intravenous injection, and inhalation) are broadly used for treatment for atopic dermatitis (particularly adult type), bronchial asthma, allergic rhinitis, etc., and an antihistaminic agent is used at the same time. There is no particular prescription for use, but it is only determined that it is used until the symptoms disappear. For this reason, recently long-term use of the agent can be often observed. Especially, a steroid agent for external use is desired to be used while gradually lowering the rank, and finally the agent is substituted by a non-steroid agent for external use. With steroid agents used for oral administration, intravenous injections or inhalations, it is desirable that these be used in the short term, but since symptoms are hardly alleviated, they are often used for a long time.

In such cases, the use of a treated product of peanut seed coats enables treatment of allergic diseases with no rebound phenomenon, even though administration of a steroid agent is terminated.

Example 2

After 1,100 mg of peanut seed coats were immersed in 100 ml of 85° C. boiled water for 1.5 minutes, the extracted blood red-colored solution was filtrated and then a bottle was filled with the filtrate. This bottle was heated at 110° C. for 10 minutes to deaerate the air contained in the solution. After deaeration, the bottle was capped with a stainless crown cap and then hermetically sealed with the cap. The hermetically capped bottle containing the solution was immersed in 90° C. boiled water for 2 hours for sterilization. The solution in the bottle became a drink having transparent blood-red color by a heating process.

Example 3

1,500 mg of peanut seed coats and 500 ml of water were placed in an earthen bottle, and were boiled with ash fire for 30 minutes to reduce the mixture to a half amount. The obtained blood red-colored solution was filtrated and the obtained extract was determined as an amount to be administered to a human per day.

Example 4

An amount of peanut seed coats was placed in 99.9% ethanol at 18° C. so that the amount subsides at 30% of alcohol volume, and left at rest for 40 days. The obtained extract was subjected to freeze-drying to obtain powder.

The thus obtained powder can directly be used as an active ingredient of the agent for treating or preventing allergic disease of the present invention.

Example 5

10 g of the powder obtained in Example 4 was mixed with 490 g of corn starch, and water was further added thereto, followed by kneading. Thereafter, the mixture was granulated with a screen having a 1 mm×1 mm mesh and dried to obtain granules.

20 mg of the powder obtained in Example 4 was included in 1 g of the granules. 5 to 10 g each of the granules was administered three times per day, depending on symptoms.

All publications, patents and patent applications cited herein are incorporated herein by reference in their entirety.

INDUSTRIAL APPLICABILITY

The present invention provides an agent effective for treatment or prevention of various allergic diseases such as pollinosis, allergic rhinitis, atopic dermatitis and bronchial asthma.

The invention claimed is:

1. A method for treating pollinosis or atopic dermatitis, said method comprising:
   administering a pharmaceutical composition, food, chewing gum or drink comprising an effective amount of a water extract of peanut seed coats, to a subject in need thereof;
   wherein the water extract is a water extract obtained at room temperature.

2. A method for treating pollinosis or atopic dermatitis, said method comprising:
   administering an affective amount of a water extract of peanut seed coats to a subject in need thereof;
   wherein the water extract is a water extract obtained at room temperature.

* * * * *